United States Patent
Sabol et al.

(10) Patent No.: US 8,401,255 B2
(45) Date of Patent: Mar. 19, 2013

(54) COMPUTER-ASSISTED RECONCILIATION OF MULTIPLE IMAGE READS

(75) Inventors: John M. Sabol, Sussex, WI (US); Gopal B. Avinash, New Berlin, WI (US); Matthew J. Walker, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 2802 days.

(21) Appl. No.: 10/323,800

(22) Filed: Dec. 18, 2002

(65) Prior Publication Data

US 2004/0120580 A1 Jun. 24, 2004

(51) Int. Cl.
*G06K 9/00* (2006.01)
*G06K 9/62* (2006.01)

(52) U.S. Cl. .................................. 382/128; 382/224

(58) Field of Classification Search .................. 382/139, 382/224, 128–134
See application file for complete search history.

(56) References Cited

U.S. PATENT DOCUMENTS

| | | | | |
|---|---|---|---|---|
| 5,359,513 A * | 10/1994 | Kano et al. | .................... | 382/128 |
| 5,537,485 A * | 7/1996 | Nishikawa et al. | ........... | 382/130 |
| 5,807,256 A * | 9/1998 | Taguchi et al. | ............... | 600/425 |
| 5,815,591 A * | 9/1998 | Roehrig et al. | ................ | 382/130 |
| 5,987,345 A * | 11/1999 | Engelmann et al. | .......... | 600/407 |
| 6,058,322 A * | 5/2000 | Nishikawa et al. | ........... | 600/408 |
| 6,556,699 B2 * | 4/2003 | Rogers et al. | ................. | 382/132 |
| 6,801,645 B1 * | 10/2004 | Collins et al. | ................. | 382/130 |
| 2003/0016850 A1 * | 1/2003 | Kaufman et al. | ............. | 382/128 |

* cited by examiner

Primary Examiner — Aaron W Carter
(74) Attorney, Agent, or Firm — Fletcher Yoder, P.C.

(57) ABSTRACT

A technique for reconciling two or more reads of an image data set. One or more computer implemented routines is employed to provide computer-assisted reconciliation (CAR) including resolution of discrepancies between the two or more reads. The computer-assisted reconciliation may optimally display the discrepancies, the concurrences and any associated information to a human reconciler, may resolve the discrepancies in a partially automated manner, or may resolve the discrepancies in a fully automated manner. The reconciled data may then be provided to an end user.

60 Claims, 7 Drawing Sheets

COMPUTER-ASSISTED RECONCILIATION OF MULTIPLE IMAGE READS

BACKGROUND OF THE INVENTION

The present technique relates generally to imaging techniques and more particularly to feature identification within digital images. Specifically the technique relates to the use of computer implemented routines to assist in the reconciliation of two or more sets of classified features in an image data set.

Various technical fields engage in some form of image evaluation and analysis in which the identification and classification of recognizable features within the image data is a primary goal. For example, medical imaging technologies produce various types of diagnostic images which a doctor or radiologist may review for the presence of identifiable features of diagnostic significance. Similarly, in other fields, other features may be of interest. For example, non-invasive imaging of package and baggage contents may similarly be reviewed to identify and classify recognizable features. In addition, the analysis of satellite and radar weather data may involve the determination of what weather formations, such as tornados or other violent storms, are either present in the image data or are in the process of forming. Likewise, evaluation of astronomical and geological data represented visually may also involve similar feature identification exercises. With the development of digital imaging and image processing techniques, the quantity of readily available image data requiring analysis in many of these technical fields has increased substantially.

Indeed, the increased amounts of available image data may inundate the human resources, such as trained technicians, available to process the data. For example, it is often desirable to have a second trained technician independently process or "read" the data. This is a rather time-consuming and expensive practice, but one that is highly valued, particularly in medical diagnostics. However, in addition to the time taken to perform the second read of the data, time is also required to compare results and to resolve any discrepancies between the independent reads such that a final interpretation of the data may be determined. These discrepancies may occur at different levels, including discrepancies in detecting a feature, segmenting the feature from the surrounding image, classifying the feature, or in regard to other distinctions associated with the feature.

The readers may meet periodically to discuss and resolve discrepancies as well as to determine those cases on which they concur. These periodic meetings also allow the readers to hone their skills by discussing and evaluating the more difficult data which generally gives rise to discrepancies. To prepare and conduct these meetings, however, valuable time may be spent combining the data and flagging the discrepancies as well as the concurrences if those are to be reviewed as well. Likewise, the presentation of data to be discussed in such a meeting may be unnecessarily complicated by the inclusion of data for which there is no discrepancy, though this information may be of interest in other contexts. In addition, the efficiency of the process may be reduced in the absence of reader notes and assessments correlated with the discrepancies, which might facilitate a rapid assessment and reconciliation of many of the discrepancies.

In addition, groups of readers, such as in a class or educational setting, may independently read an image data set as part of the educational process. Feedback regarding performance in such an educational setting may be most productively focused on the discrepancies between independent reads and not on data where there is little, if any, disagreement. Likewise, panels of experts may also independently read an image data set in order to provide a consensus interpretation of the data, which may be used to train automated detection and classification routines such as those used in computer-assisted detection (CAD) algorithms. To the extent such expert panels are also evaluating difficult data, presumably the data most likely to cause problems for automated routines, a streamlined reconciliation process may also be beneficial.

BRIEF DESCRIPTION OF THE INVENTION

The present invention provides a technique for reconciling the results of independent image evaluation processes or "reads." The technique creates an integrated result set from the various reads and may include additional information provided by each reader, such as notes and probability assessments. The various reads may be reconciled, with discrepancies between the reads being resolved by one or more reconcilers. Any notes or probability assessments relevant to a discrepancy under review may also be provided during the discrepancy resolution process to enhance and improve the reconciliation process. In the absence of any disagreements between the two or more reads, a notice may simply be provided to the relevant parties to indicate that no further review is needed.

In accordance with one aspect of the present technique, a method for reconciling two or more reads of a set of image data is provided. Two or more reads of an image data set provided by two or more respective readers are integrated. One or more discrepancies or concurrences exist between the two or more reads. An integrated data set is formed comprising the one or more discrepancies or concurrences.

In accordance with another aspect of the present technique, a method for reconciling two or more reads of a set of image data is provided. Two or more reads of an image data set provided by two or more respective readers are integrated. One or more discrepancies exist between the two or more reads. The one or more discrepancies are resolved by application of one or more automated routines.

In accordance with an addition aspect of the present technique, an image analysis system is provided. The image analysis system includes an imager and system control circuitry configured to operate the imager. In addition, the system includes data acquisition circuitry configured to access an image data set acquired by the imager. An operator interface configured to interact with at least one of the system control circuitry and the data processing circuitry is included. The operator interface is further configured to allow an operator to view one or more discrepancies or concurrences present in an integrated data set and to resolve the one or more discrepancies. Data processing circuitry is also included and is configured to integrate two or more reads of the image data set provided by two or more respective readers to form the integrated data set comprising the one or more discrepancies or concurrences between the two or more reads.

In accordance with a further aspect of the present technique, an image analysis system is provided. The image analysis system includes an imager and system control circuitry configured to operate the imager. In addition, the system includes data acquisition circuitry configured to access an image data set acquired by the imager. An operator interface configured to interact with at least one of the system control circuitry and the data processing circuitry is included. Data processing circuitry is also included and is configured to integrate two or more reads of an image data set provided by two or more respective readers wherein one or more discrepancies exist between the two or more reads. The data processing circuitry is further configured to resolve the one or more discrepancies by application of one or more automated routines.

In accordance with an additional aspect of the present technique, an image analysis system is provided. The image analysis system includes an imager and system control circuitry configured to operate the imager. In addition, the system includes data acquisition circuitry configured to access an image data set acquired by the imager. An operator interface configured to interact with at least one of the system control circuitry and the data processing circuitry is included. Data processing circuitry is also included and is configured to process the image data set accessed by the data acquisition circuitry and to generate images for display on the operator interface. The system also includes means for resolving discrepancies between two or more reads of the image data set generated by two or more respective readers.

In accordance with an additional aspect of the present technique, an image analysis system is provided. The image analysis system includes an imager and system control circuitry configured to operate the imager. In addition, the system includes data acquisition circuitry configured to access an image data set acquired by the imager. An operator interface configured to interact with at least one of the system control circuitry and the data processing circuitry is included. Data processing circuitry is also included and is configured to process the image data set accessed by the data acquisition circuitry and to generate images for display on the operator interface. The system also includes means for reconciling two or more reads of the image data set generated by two or more respective readers.

In accordance with another aspect of the present technique, a tangible medium is provided for reconciling two or more reads of a set of image data. The tangible medium includes a routine for integrating two or more reads of an image data set provided by two or more respective readers. One or more discrepancies or concurrences exist between the two or more reads. Also included is a routine for forming a resolution data set comprising the one or more discrepancies or concurrences.

In accordance with another aspect of the present technique, a tangible medium is provided for reconciling two or more reads of a set of image data. The tangible medium includes a routine for integrating two or more reads of an image data set provided by two or more respective readers. One or more discrepancies exist between the two or more reads. Also included is a routine for automatically resolving the one or more discrepancies.

In accordance with an additional aspect of the present invention, a method is provided for reconciling two or more reads of a set of image data. Two or more reads of an image data set provided by two or more respective readers are integrated to form an integrated data set comprising one or more features. The one or more features of the integrated data set are reconciled, at least partially via an automated algorithm, to form a final classification image.

In accordance with another aspect of the present invention, a method is provided for reviewing two or more reads of a set of image data. Two or more reads of an image data set provided by two or more respective readers are automatically compared. A notice based upon the comparison is generated.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

The present technique pertains to the computer-assisted reconciliation of multiple reads of digital image data of various sorts, including analog image data that has been digitized. For simplicity, and in accordance with a presently contemplated implementation, the following example discusses the technique in the context of medical imaging. However it is to be understood that the technique is not limited to medical imaging. Instead, any digital imaging implementation in which more than one reader evaluates image data for features of interest which may or may not be subsequently classified, may benefit from the following technique. Digital image data of a general or technical nature that may employ computer implemented routines to assist in the reconciliation of independent evaluation results may benefit from the present technique. Examples of such digital image data include, but are not limited to, meteorological, astronomical, geological, and medical data, as well as baggage and package screening data.

Figure 1:
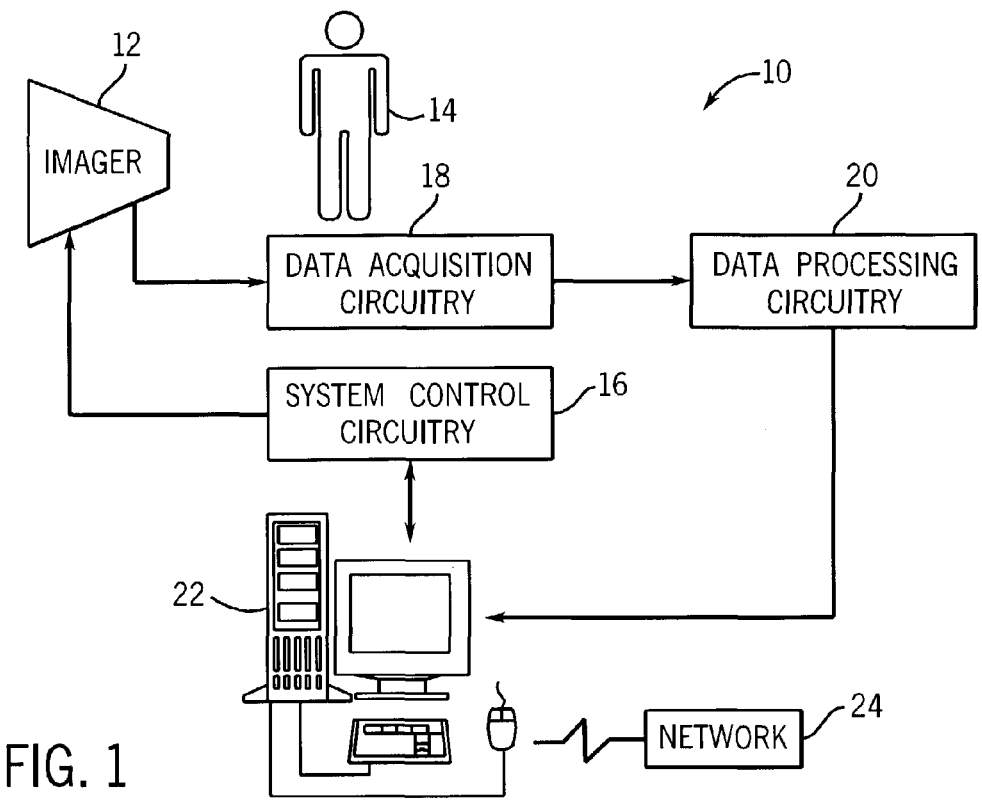
FIG. 1 is a general diagrammatical representation of certain functional components of an exemplary image data-producing system, in the form of a medical diagnostic imaging system.

In the context of medical imaging, various imaging resources may be available for diagnosing medical events and conditions in both soft and hard tissue, and for analyzing features and function of specific anatomies. FIG. 1 provides a general overview for exemplary imaging systems, and subsequent figures offer somewhat greater detail into the major system components of a specific modality system. Such medical imaging systems may include, but are not limited to, medical imaging modalities such as digital X-ray, Computed Tomography (CT), Magnetic Resonance Imaging (MRI), Positron Emission Tomography (PET), thermoacoustic imaging, optical imaging, and nuclear medicine-based imaging.

Referring to FIG. 1, an imaging system 10 generally includes some type of imager 12 which detects signals and converts the signals to useful data. As described more fully below, the imager 12 may operate in accordance with various physical principles for creating the image data. In general, however, in the medical imaging context image data indicative of regions of interest in a patient 14 are created by the imager in a digital medium.

The imager 12 operates under the control of system control circuitry 16. The system control circuitry may include a wide range of circuits, such as radiation source control circuits, timing circuits, circuits for coordinating data acquisition in conjunction with patient or table of movements, circuits for controlling the position of radiation or other sources and of detectors, and so forth. The imager 12, following acquisition of the image data or signals, may process the signals, such as for conversion to digital values, and forwards the image data to data acquisition circuitry 18. In digital systems, the data acquisition circuitry 18 may perform a wide range of initial processing functions, such as adjustment of digital dynamic ranges, smoothing or sharpening of data, as well as compiling of data streams and files, where desired. The data are then transferred to data processing circuitry 20 where additional processing and analysis are performed. For the various digital imaging systems available, the data processing circuitry 20 may perform substantial analyses of data, ordering of data, sharpening, smoothing, feature recognition, and so forth.

Ultimately, the image data are forwarded to some type of operator interface 22 for viewing and analysis. While operations may be performed on the image data prior to viewing, the operator interface 22 is at some point useful for viewing reconstructed images based upon the image data collected. The images may also be stored in short or long-term storage devices, for the present purposes generally considered to be included within the interface 22, such as picture archiving communication systems. The image data can also be transferred to remote locations, such as via a network 24. It should also be noted that, from a general standpoint, the operator interface 22 affords control of the imaging system, typically through interface with the system control circuitry 16. Moreover, it should also be noted that more than a single operator interface 22 may be provided. Accordingly, an imaging scanner or station may include an interface which permits regulation of the parameters involved in the image data acquisition procedure, whereas a different operator interface may be provided for manipulating, enhancing, and viewing resulting reconstructed images.

Figure 2:
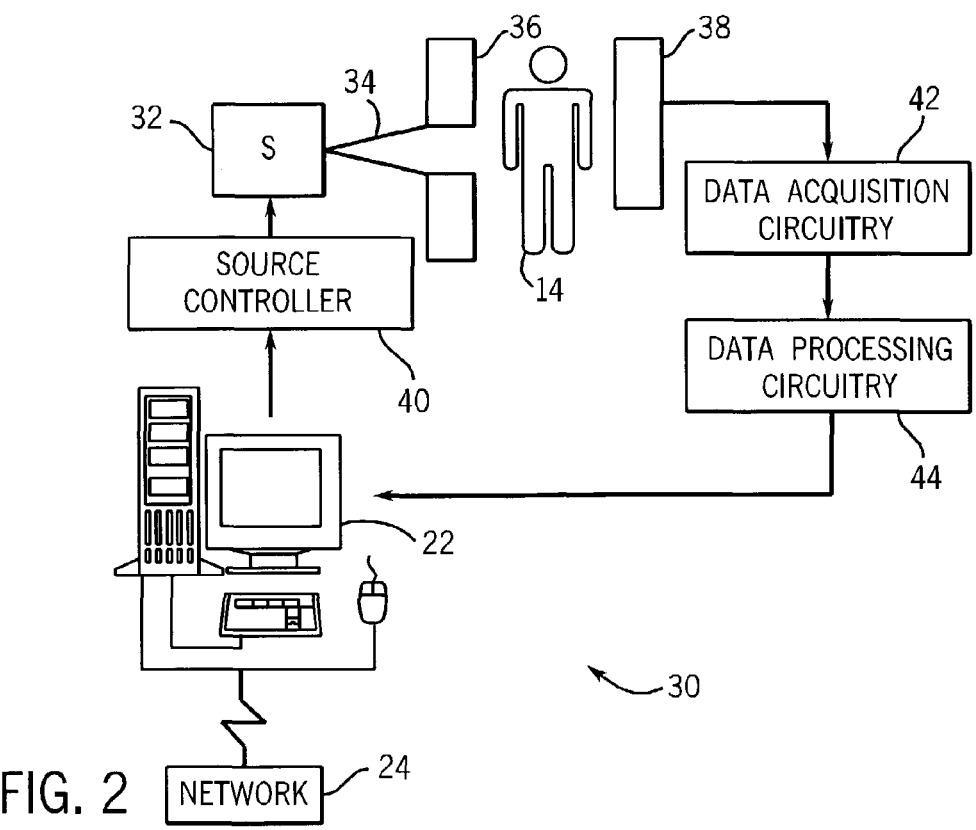
FIG. 2 is a diagrammatical representation of a particular imaging system of the type shown in FIG. 1, in this case an exemplary X-ray imaging system which may be employed in accordance with certain aspects of the present technique.

To discuss the technique in greater detail, a specific medical imaging modality based upon the overall system architecture outlined in FIG. 1 is depicted in FIG. 2. FIG. 2 generally represents a digital X-ray system 30. System 30 includes a radiation source 32, typically an X-ray tube, designed to emit a beam 34 of radiation. The radiation may be conditioned or adjusted, typically by adjustment of parameters of the source 32, such as the type of target, the input power level, and the filter type. The resulting radiation beam 34 is typically directed through a collimator 36 which determines the extent and shape of the beam directed toward patient 14. A portion of the patient 14 is placed in the path of beam 34, and the beam impacts a digital detector 38.

Detector 38, which typically includes a matrix of pixels, encodes intensities of radiation impacting various locations in the matrix. A scintillator converts the high energy X-ray radiation to lower energy photons which are detected by photodiodes within the detector. The X-ray radiation is attenuated by tissues within the patient, such that the pixels identify various levels of attenuation resulting in various intensity levels which will form the basis for an ultimate reconstructed image.

Control circuitry and data acquisition circuitry are provided for regulating the image acquisition process and for detecting and processing the resulting signals. In particular, in the illustration of FIG. 2, a source controller 40 is provided for regulating operation of the radiation source 32. Other control circuitry may, of course, be provided for controllable aspects of the system, such as a table position, radiation source position, and so forth. Data acquisition circuitry 42 is coupled to the detector 38 and permits readout of the charge on the photo detectors following an exposure. In general, charge on the photo detectors is depleted by the impacting radiation, and the photo detectors are recharged sequentially to measure the depletion. The readout circuitry may include circuitry for systematically reading rows and columns of the photo detectors corresponding to the pixel locations of the image matrix. The resulting signals are then digitized by the data acquisition circuitry 42 and forwarded to data processing circuitry 44.

The data processing circuitry 44 may perform a range of operations, including adjustment for offsets, gains, and the like in the digital data, as well as various imaging enhancement functions. The resulting data are then forwarded to an operator interface or storage device for short or long-term storage. The images reconstructed based upon the data may be displayed on the operator interface, or may be forwarded to other locations, such as via a network 24, for viewing. Also, digital data may be used as the basis for exposure and printing of reconstructed images on a conventional hard copy medium such as photographic film.

When in use, the digital X-ray system 30 acquires digital X-ray images of a portion of the patient 14 which may then be analyzed for the presence of indicia of one or more medical pathologies such as nodules, lesions, fractures, microcalcifications, etc. Other imaging modalities of course may be better suited for detecting different types of anatomical features. In practice, a clinician, herein referred to as a first reader, may initially review a medical image, such as an X-ray, and detect features or features of diagnostic significance within the image. The first reader may then assign a classification to each feature. For reasons of quality assurance, a second clinician, herein referred to as a second reader, may independently review the medical image and detect and classify features in the image. Discrepancies between the detections and classifications of the first and second readers can then be reconciled via mutual consultation or some predetermined resolution mechanism, such as some prioritizing criterion or third party consultation. In other contexts, such as clinician training or panel review of data for the "training" of automated routines, additional independent readers may be present beyond the two commonly present in the quality control context. It should also be understood that a reader may be a human, such as a trained clinician, or an automated routine, such as a CAD routine comprising one or more specialized modules for the detection, the classification, or the segmentation of features within an image data set.

The net effect of these different levels of independent review is to improve the overall quality of the analysis and subsequent diagnosis. In particular, the use of independent reviews is ultimately directed toward reducing the incidence of false positives, i.e. indicating a pathological condition when none is present, and false negatives, i.e. failing to indicate a pathological condition when one is present. An undesired consequence of the independent reads, however, is the time required to perform these redundant reviews. In addition, in the event that the discrepancies exist between the first and second reads, additional time is required to combine and reconcile the independent reads.

The periodic sessions during which the readers reconcile the discrepancies may involve both readers analyzing the complete result sets to locate discrepancies. In addition, the reconciliation session may occur several days, or even later, after the initial reads were performed, which may make it difficult for a reader to recreate the thought processes which contributed to a feature detection or classification. As a result, the reconciliation session may be less efficient, particularly in the time consumed, than is desirable. One technique which utilizes a computer-assisted reconciliation (CAR) technique to improve the efficiency associated with the reconciliation of two or more reads is depicted in FIG. 3.

Figure 3:
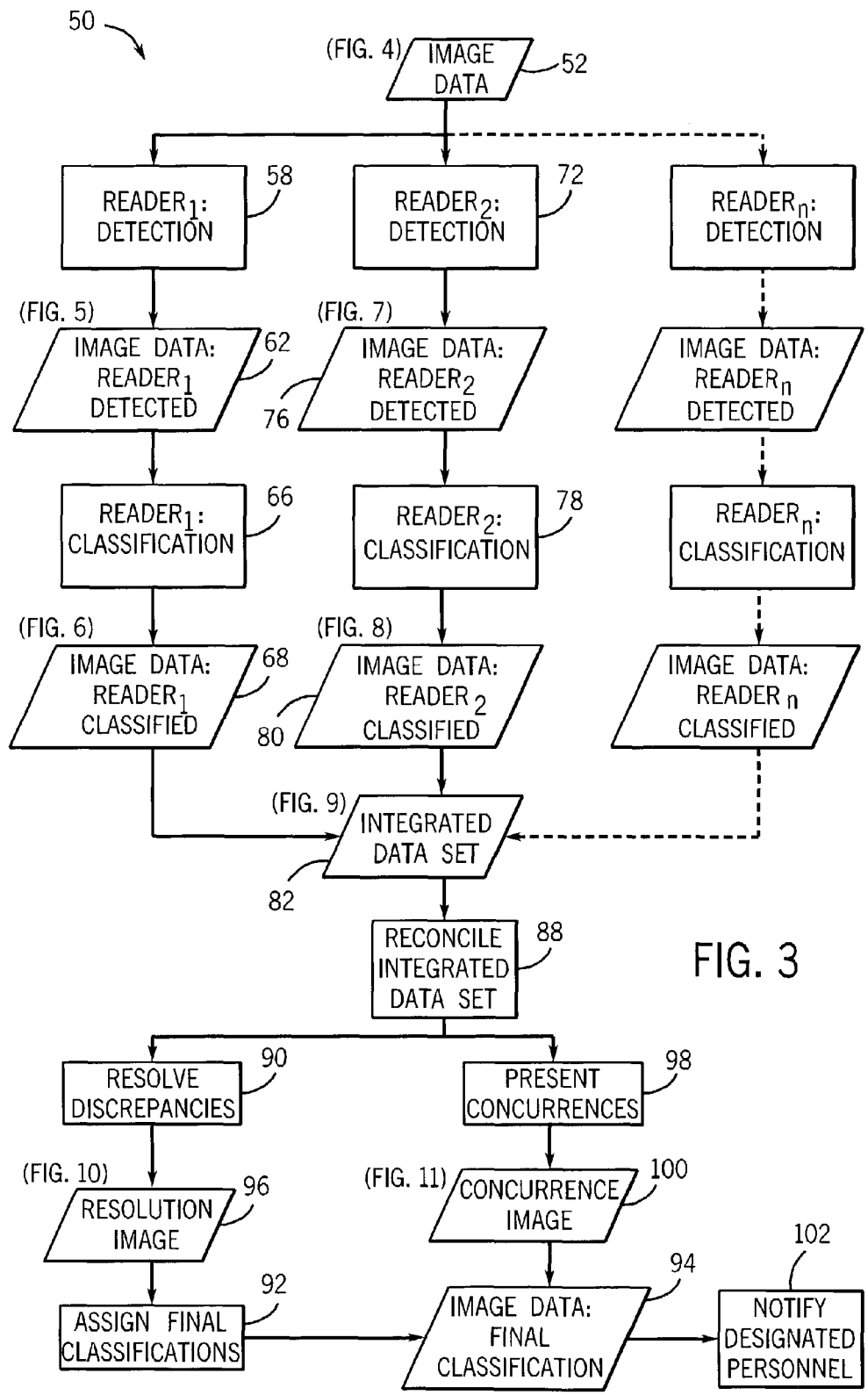
FIG. 3 is a flowchart depicting an embodiment of the present technique utilizing computer-assisted reconciliation.
Figure 4:
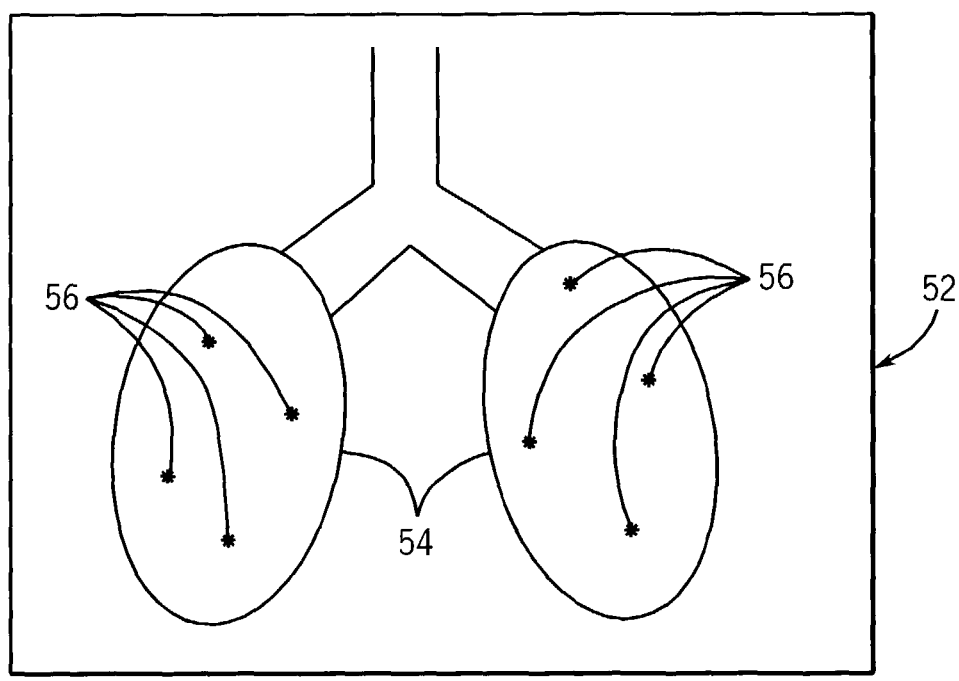
FIG. 4 is a representation of a set of medical image data including features to be detected and classified.

As depicted in FIG. 3, the image review process 50 begins with an initial set of image data 52 such as may be acquired by a system like the digital X-ray imaging system 30 of FIG. 2. For the purposes of example only, the image data 52 are depicted in greater detail in FIG. 4 as a digital X-ray image of a pair of lungs 54 possessing various features 56 of interest. This image data may be initially read by a human agent, such as a physician, clinician, or radiologist, or by an automated routine, such as a CAD algorithm, to detect features 56, as indicated at step 58. The image data set 52 along with the first detected features 60 constitute a first detected data set 62, as depicted in FIG. 5.

Figure 5:
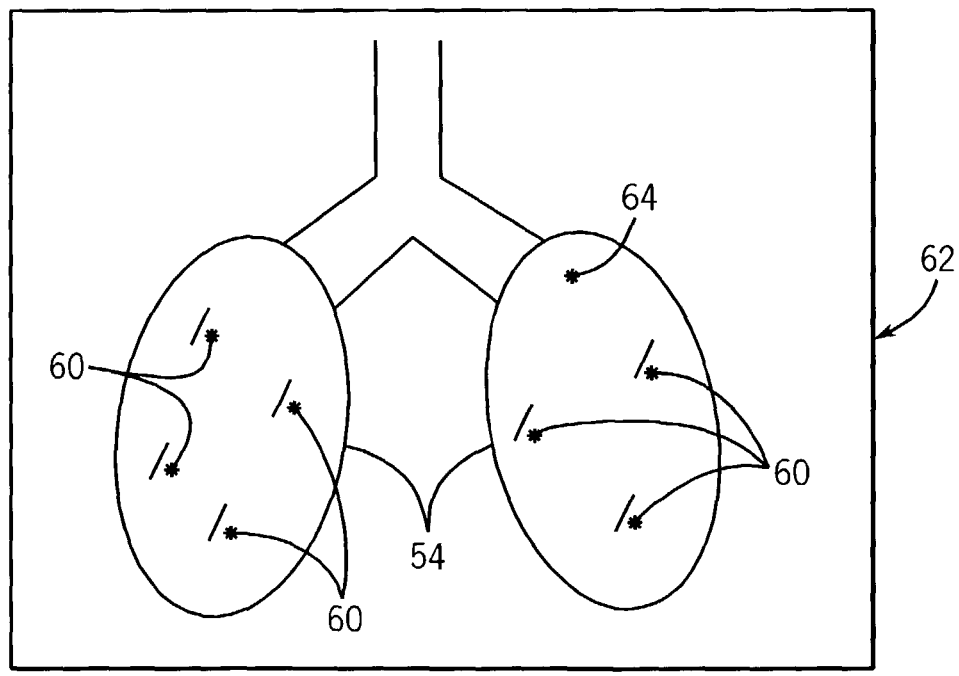
FIG. 5 is a representation of the set of medical image data of FIG. 4 after feature detection by a first reader.

As depicted in FIG. 5, the first detected image data set 62 includes features detected by the first reader, i.e. first detected features 60, signified by an adjacent forward-slash (/). The data set 62 may also include unidentified features 64 missed by the missed first reader. Various graphical indicia, text, overlays, colors, highlighting, and so forth may serve to indicate the detected features 60 if displayed. Also potentially present, though not illustrated here, are falsely identified features, which are non-features the first reader incorrectly identifies as features 56.

Figure 6:
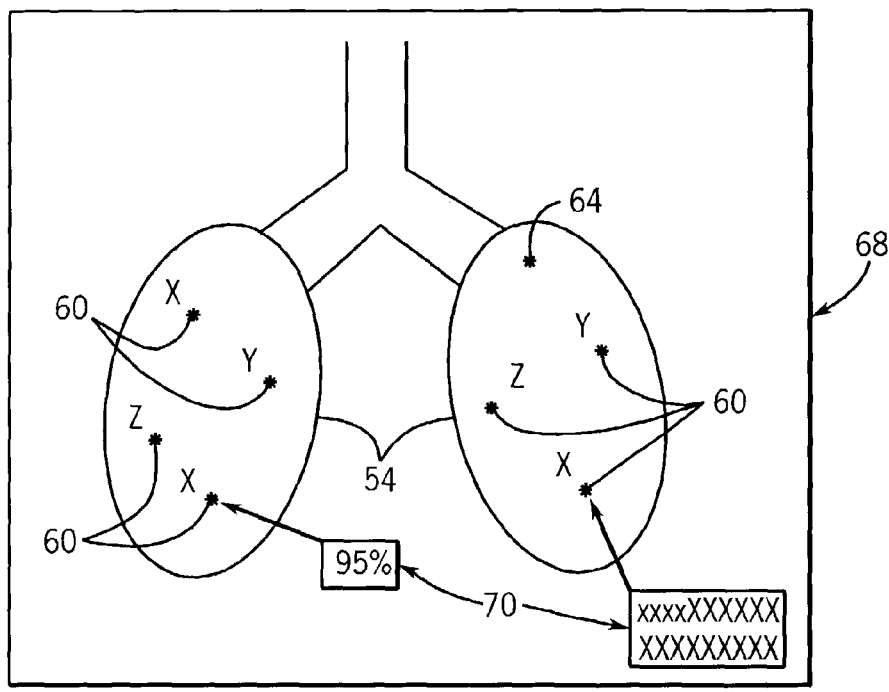
FIG. 6 is a representation of the set of medical image data of FIG. 5 after feature classification by a first reader.

The detected features 60 are subsequently classified by the first reader, as indicated at step 66 of FIG. 3, to produce a first classified data set 68, as depicted in FIG. 6. The first classification is here represented variously by the letters X, Y, and Z in FIG. 6, to represent various classifications which may be assigned by the first reader. The first reader may also assign one or more information cues 70 associated with the assigned classification during the classification process of step 66 which may be available during subsequent processes such as reconciliation or diagnosis. These cues 70 may include, but are not limited to, measures of probability or certainty, possibly including probabilities of malignancy. In addition, the cues 70 may also include one or more visual cues, such as text, highlighting or color coding, or audible notes with each classified feature for later reference. In addition, the first reader may perform other analyses of the data such as feature segmentation in which the region of the image believed to constitute the feature is separated from the surrounding image, such as by drawing borders or boundaries associated with the feature.

A separate, independent read of the image data 52 may be performed by a second reader for quality purposes. The second read may include feature detection as well as feature classification or segmentation. For simplicity, the second reader is discussed in detail though, of course, additional readers may be present, as depicted in FIG. 3. Additional readers may be processed in accordance with the following discussion.

Figure 7:
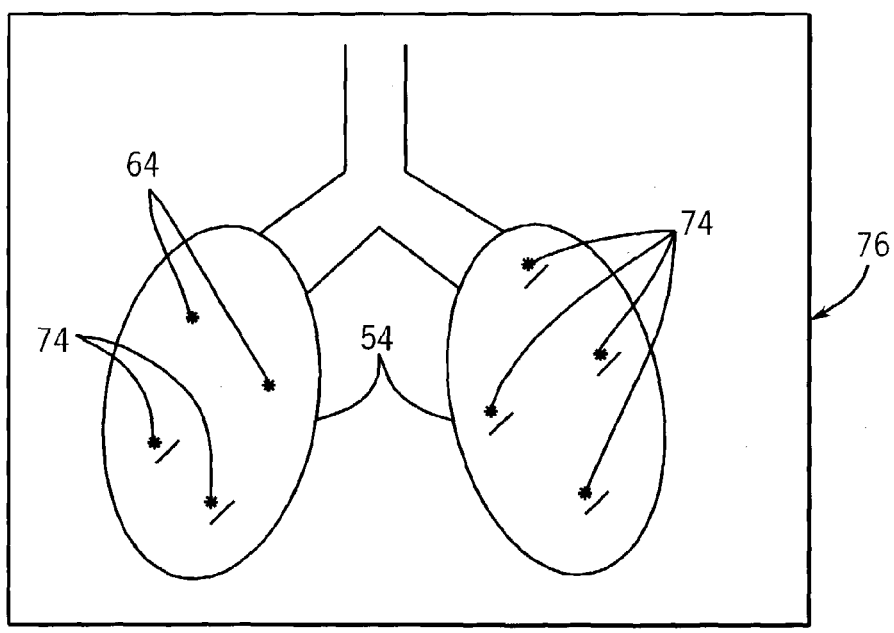
FIG. 7 is a representation of the set of medical image data of FIG. 4 after feature detection by a second reader.

The second reader, as depicted at step 72 detects features 56 in the image data set 52. The features detected by the second reader, i.e., the second detected features 74, as well as any undetected features 64 comprise a second detected data set 76, as depicted in FIG. 7. As depicted in FIG. 7, the second detected features 74 are signified by an adjacent forward-slash (/). Various graphical indicia, text, overlays, colors, highlighting, and so forth may serve to indicate the second detected features 74 if displayed. Also potentially present, though not illustrated here, are falsely identified features, which are non-features the second reader incorrectly identifies as features 56.

Figure 8:
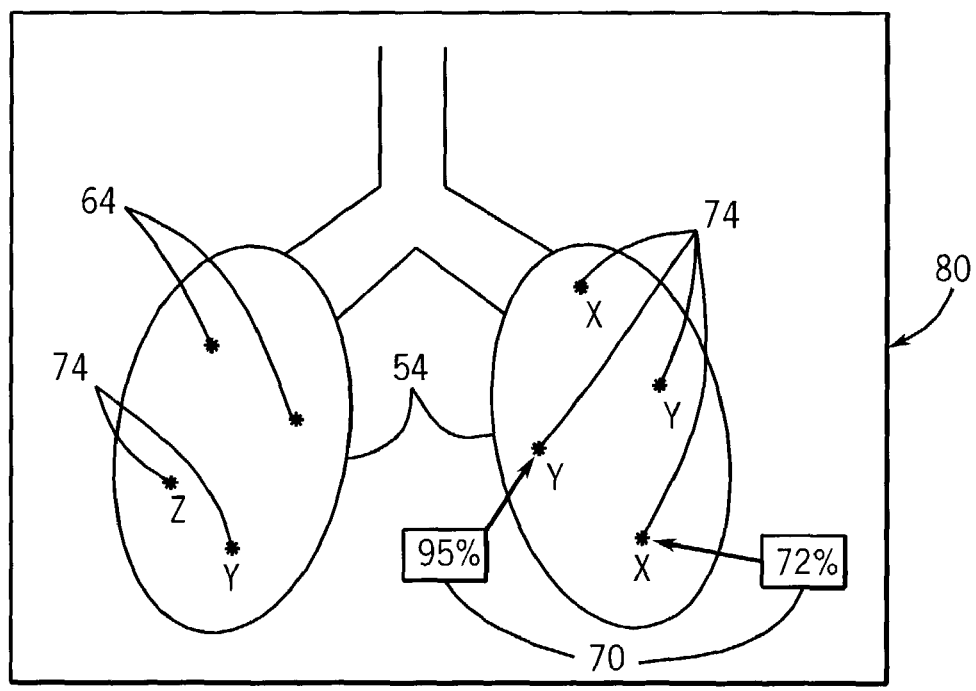
FIG. 8 is a representation of the set of medical image data of FIG. 7 after feature classification by a second reader.

The second reader may then classify the second detected features 74, as provided at step 78, of the second detected data set 76. A second classified data set 80, depicted in FIG. 8, results from the classification step 78. As with the first classification, the second classification is also represented variously by the letters X, Y, and Z in FIG. 8, which represent the various classifications that may be assigned by the second reader. The second reader may also assign one or more information cues 70 associated with the assigned classification during the classification process of step 78 for subsequent reference.

Figure 9:
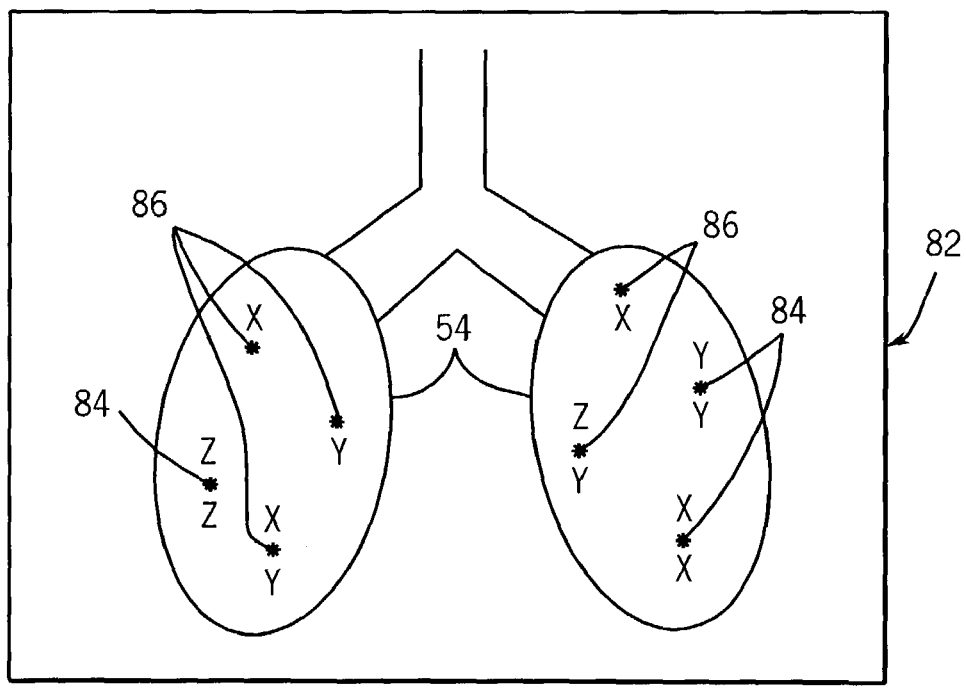
FIG. 9 is a representation of the set of medical image data of FIGS. 6 and 8 after integration.

The first classified data set 68 and second classified data set 80 may be combined to form an integrated data set 82, as depicted in FIG. 9. An example of such an integrated data set 82 might simply be a union data set created from the first and second classified data sets 68 and 80 respectively. As will be noted, the integrated data set 82 may include concordant features 84, in which the first and second detections and classifications, as well as any additional reader assigned values, such as segmentation, probabilities, etc., agree. In addition, the integrated data set may include discordant features 86 in which the there is disagreement, i.e., a discrepancy, between the first and second reader regarding the detection or classification or some other assigned characteristic of a feature 56.

The integrated data set 82 may be reconciled, as depicted at block 88 to coordinate the results of the various reads. For example, if discrepancies exist between the first and second reads, as determined by the presence of discordant features 86 in the integrated data set 82, these discrepancies may be resolved, as depicted as step 90. The resolution process resolves disagreements between the various readers, assigning a final classification to each discordant feature 86, as depicted at step 92, and contributing to a final classification image data set 94. In the present technique, the computer-assisted reconciliation (CAR) process may fully automated, partially automated, or may otherwise perform automated routines to assist a reconciler or other viewers, such as in the display of discrepancies, concurrences, and associated information.

Figure 10:
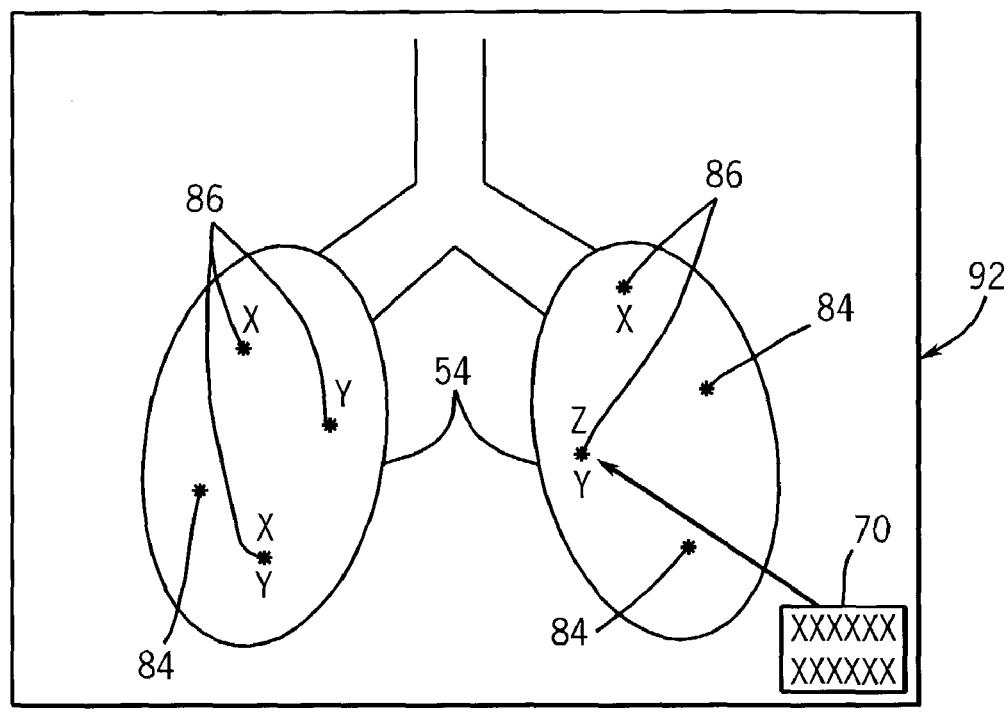
FIG. 10 is a representation of the set of medical image data of FIG. 9 displaying discrepancies to be reconciled.

For example, to aid in resolving discrepancies, the CAR process may mask the concordant features 84 to form a resolution image 96 (depicted in FIG. 10). In particular, the concordant features 84 may be masked to simplify the presentation of the integrated data set 82 for a human reconciler performing the resolution process of step 90. In a fully or partially automated reconciliation process, the computer implemented reconciliation routine might also utilize the resolution image 96, or a logical equivalent, or might simply operate on discordant features 86 present in the integrated image 82.

In the resolution process of step 90, the information available to the reconciler, whether a human or a computer routine, may include the detection and the classification of each discordant feature 86 as provided by the various reads in addition to any other discrepancies to be resolved, such as segmentation. To aid the reconciler, particularly a human reconciler, the detections and classifications provided by the various readers may be differentiated graphically, such as by color, position, shading, markers, and so forth.

The reconciler may also be provided with the various information cues 70 provided by the various readers which may provide information regarding probabilities and certainty of the classification or other, non-statistical information which may aid the reconciler. The information cues 70 may be automatically displayed or interactively displayed upon a request by the reconciler. For example, the information cues 70 may be provided as interactive pop-up text or numerics which may be opened by moving a cursor over a discordant feature 86 and closed by moving the cursor away. In another embodiment, text, numerics or other forms of information cues may simply be displayed for each discordant feature 86 needing reconciliation and removed as the reconciler processes that discordant feature 86.

In addition to notes and probabilities provided by the readers, the information cues 70 may also provide information obtained from an information medical knowledge base, such as individual and family medical history, genetic predispositions, demographic data, prior diagnoses, pharmacological history, and journal or text articles or tables. While text, interactive or otherwise, is one form of possible information cue 70 other visual or audible indicators may also be provided. For example various classifications, statistical data, CT settings, or other relevant data may be conveyed by color-coding, gray-shading, geometric shapes, differential intensity and so forth which convey the information in a relatively simple and concise manner. Likewise, audible cues, such as an audible portion of a medical text or database, may be utilized and may be interactively invoked by a human reconciler, such as by moving a cursor over a discordant feature 86. In general, the information cues provide quantitative or qualitative information, either visually or audibly, to a reconciler or subsequent diagnostician regarding the classification of a feature 56.

In fully automated reconciliation, the final classification of a discordant feature 86 may be assigned by an automated process such as automated implementation of a set of hierarchical rules. The rule-based evaluation may be automatically implemented for each discordant feature 86 and may evaluate such factors as any probabilities assigned by the various readers, historic performance of the various readers, or factors contained in an integrated medical knowledge base. For example, one such a rule may be to accept the classification provided by a human reader over that provided by an automated algorithm in instances where the human reader has indicated a greater degree of certainty than the automated algorithm.

A partially automated CAR process may employ the same or similar routines to a fully automated CAR process but may in addition rely upon input from a human reconciler, i.e., recommendations or approvals, prior to assigning a final classification. For example, a partially automated CAR process might only assign an advisory classification to each discordant feature 86 pending final acceptance by a human agent.

Figure 11:
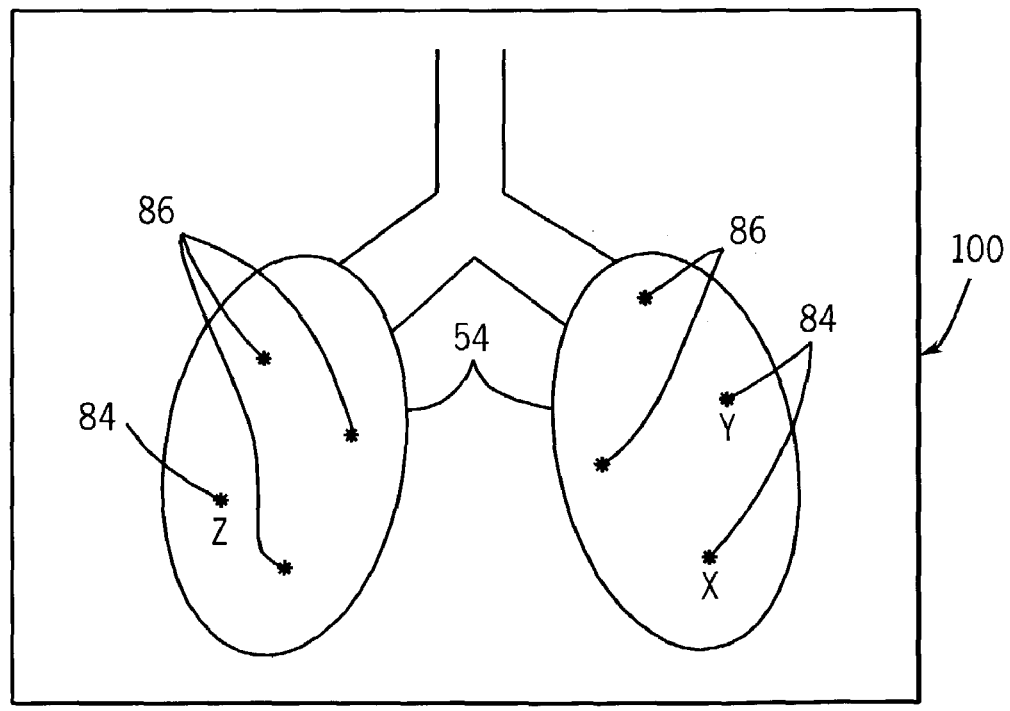
FIG. 11 is a representation of the set of medical image data of FIG. 9 displaying detection and/or classification concurrences.

In addition to the discrepancy resolution which may occur as part of the reconciliation process, reconciler or readers may also desire to evaluate any concurrences between the various reads, i.e. concordant features 84. Therefore the reconciliation process may optionally include a step 98 for presenting the information between from the various reads for which there is agreement. The concurrences may be presented to human viewers as a concurrence image 100, as depicted in FIG. 11, which may mask out discordant features to be reconciled and may simplify the presentation of the concordant data in order to facilitate review. As with the resolution image 96, information cues 70 may be provided to a viewer to supply any available information regarding the displayed features.

While separate and distinct concurrence and resolution images, 100 and 96 respectively, have been discussed for simplicity, these images need not actually be separate. Indeed, the integrated data set 82 may simply be adapted to clearly differentiate the discordant features 86 in need of resolution from concordant features 84 presented for information. This differentiation may be by color coding, shading, flags and markers, or other forms of visual cues.

Figure 12:
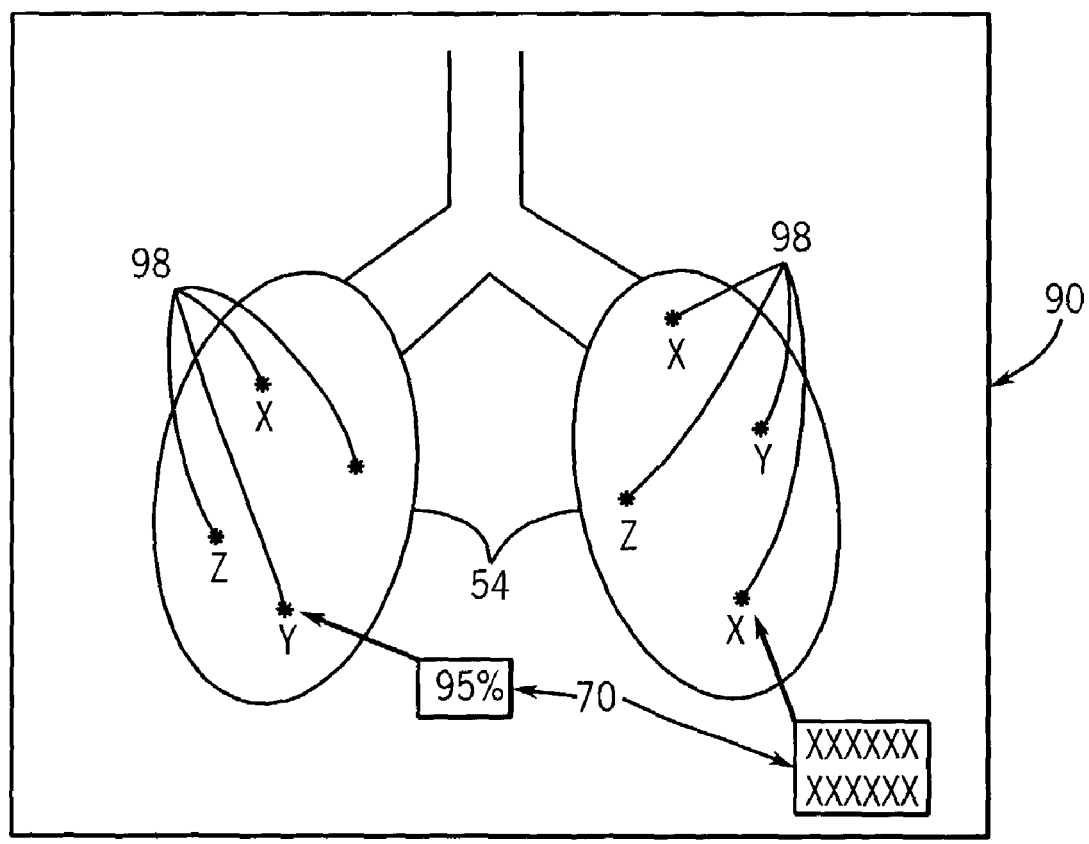
FIG. 12 is a representation of the set of medical image data of FIG. 9 after reconciliation.

The result of the reconciliation processing is a final classification image data set 94, as depicted in FIG. 12, in which each discordant feature 86 has been assigned a final classification or is determined to not be a feature of interest and in which any reconciled concordant features 84 may also presented.

The final classification image data set 94 may be provided to a clinician or physician for use in diagnosing and treating the patient 14. As with the integrated data set 82, information cues 70 may be provided in the final classification image data set 94 to assist a viewer in evaluating the diagnostic significance of the reconciled features 104. The information cues 70 may include particular information about the reconciled feature 104, projected prognosis information, probability of malignancy, statistical information regarding the certainty of the classification, or more general information about that class of feature such as might be accessed in a medical text or journal or integrated medical knowledge base.

After the reconciliation processing and the formation of the final classification image data set 94, any designated personnel, such as readers, physicians, or other technical personnel, may receive a notice of the results, as depicted at step 102, such as by displayed message, e-mail, result report, and so forth. In addition, though not depicted, a notice may also be issued to the designated personnel in the event that no features are detected by the various readers or if, in the integrated data set 82, there is complete concurrence between the various readings. In these instances, no further images may be displayed due to the absence of detected features or of disagreement. The notice, therefore, may conclude the review process by providing the relevant information, such as no detected features, concurrence for all detected features, etc., to the necessary personnel.

While the invention may be susceptible to various modifications and alternative forms, specific embodiments have been shown by way of example in the drawings and have been described in detail herein. However, it should be understood that the invention is not intended to be limited to the particular forms disclosed. In particular, though the discussed embodiments relate to medical imaging, it is to be understood than other forms of technical image analysis and non-invasive imaging, such as baggage and package screening, as well as meteorological, astronomical, geological, and non-destructive material inspection image analysis, may benefit from the discussed technique. Indeed, any form of digital image processing in which features of interest are detected and/or classified may benefit from this technique. The invention is to cover all modifications, equivalents, and alternatives falling within the spirit and scope of the invention as defined by the following appended claims.

What is claimed is:

1. A method, comprising:
   integrating two or more reads of an image data set provided by two or more respective readers, wherein one or more discrepancies exist between the two or more reads; and
   resolving the one or more discrepancies by application of one or more automated routines.

2. The method as recited in claim 1, wherein the two or more respective readers include at least one automated algorithm.

3. The method as recited in claim 1, wherein the discrepancies include at least one of a detection discrepancy or a classification discrepancy.

4. The method as recited in claim 1, further comprising acknowledging the resolution results provided by the one or more automated routines.

5. The method as recited in 1, further comprising forming a resolution image.

6. The method as recited in claim 5, wherein the resolution image includes one or more information cues associated with one or more discordant features.

7. The method as recited in claim 6, wherein the information cue relates at least one of a statistical measure, a classification description, or a prognosis assessment.

8. The method as recited in claim 6, wherein the information cue comprises at least one of a visual marker, a text-based message, a numeric assessment, a color coding, or a differential shading.

9. The method as recited in claim 6, wherein the information cue is provided in response to an action by a viewer.

10. An image analysis system, comprising:
an imager;
system control circuitry configured to operate the imager;
data acquisition circuitry configured to access an image data set acquired by the imager;
an operator interface configured to interact with at least one of the system control circuitry or the data processing circuitry and further configured to allow an operator to view one or more discrepancies or concurrences present in an integrated data set and to resolve the one or more discrepancies; and
data processing circuitry configured to integrate two or more reads of the image data set provided by two or more respective readers to form the integrated data set comprising the one or more discrepancies or concurrences between the two or more reads.

11. The image analysis system as recited in claim 10, wherein the two or more respective readers include at least one automated algorithm.

12. The image analysis system as recited in claim 11, wherein the data processing circuitry is further configured to run the at least one automated algorithm.

13. The image analysis system as recited in claim 10, wherein the discrepancies include at least one of a detection discrepancy or a classification discrepancy.

14. The image analysis system as recited in claim 10, wherein the concurrences include at least one of a detection concurrence or a classification concurrence.

15. The image analysis system as recited in claim 10, wherein the data processing circuitry is further configured to mask one or more features upon which the one or more reads agree.

16. The image analysis system as recited in claim 10, wherein the operator interface is further configured to display one or more information cues associated with the one or more discrepancies or concurrences.

17. The image analysis system as recited in claim 16, wherein the information cue relates at least one of a statistical measure, a classification description, a prognosis assessment, or a classification provided by a reader.

18. The image analysis system as recited in claim 16, wherein the information cue comprises at least one of a visual marker, a text-based message, a numeric assessment, a color coding, or a differential shading.

19. The image analysis system as recited in claim 16, wherein the information cue is provided in response to an action by a reconciler.

20. An image analysis system, comprising:
an imager;
system control circuitry configured to operate the imager;
data acquisition circuitry configured to access an image data set acquired by the imager;
an operator interface configured to interact with at least one of the system control circuitry or the data processing circuitry; and
data processing circuitry configured to integrate two or more reads of an image data set provided by two or more respective readers, wherein one or more discrepancies exist between the two or more reads, and to resolve the one or more discrepancies by application of one or more automated routines.

21. The image analysis system as recited in claim 20, wherein the two or more respective readers include at least one automated algorithm.

22. The image analysis system as recited in claim 21, wherein the data processing circuitry is further configured to run the at least one automated algorithm.

23. The image analysis system as recited in claim 20, wherein the discrepancies include at least one of a detection discrepancy or a classification discrepancy.

24. The image analysis system as recited in claim 20, wherein the operator interface is further configured to allow an operator to acknowledge the resolution results provided by the one or more automated routines.

25. The image analysis system as recited in claim 20, wherein the operator interface is further configured to display a resolution image generated by the one or more automated routines comprising one or more discordant or concordant features.

26. The image analysis system as recited in claim 25, wherein the operator interface is further configured to display one or more information cues associated with the one or more discordant or concordant features.

27. The image analysis system as recited in claim 26, wherein the information cue relates at least one of a statistical measure, a classification description, or a prognosis assessment.

28. The image analysis system as recited in claim 26, wherein the information cue comprises at least one of a visual marker, a text-based message, a numeric assessment, a color coding, or a differential shading.

29. The image analysis system as recited in claim 26, wherein the information cue is provided in response to an action by a viewer.

30. An image analysis system, comprising:
an imager;
system control circuitry configured to operate the imager;
data acquisition circuitry configured to access an image data set acquired by the imager;
an operator interface configured to interact with at least one of the system control circuitry or the data processing circuitry;
data processing circuitry configured to process the image data set accessed by the data acquisition circuitry and to generate images for display on the operator interface; and
means for resolving discrepancies between two or more reads of the image data set generated by two or more respective readers.

31. An image analysis system, comprising:
an imager;
system control circuitry configured to operate the imager;
data acquisition circuitry configured to access an image data set acquired by the imager;
an operator interface configured to interact with at least one of the system control circuitry or the data processing circuitry;

data processing circuitry configured to process the image data set accessed by the data acquisition circuitry and to generate images for display on the operator interface; and means for reconciling two or more reads of the image data set generated by two or more respective readers.

32. A machine-readable medium, comprising:
a routine for integrating two or more reads of an image data set provided by two or more respective readers, wherein one or more discrepancies or concurrences exist between the two or more reads; and
a routine for forming a resolution data set comprising the one or more discrepancies or concurrences,
wherein the routine for forming the resolution data set excludes one or more concurrences.

33. The machine-readable medium as recited in claim 32, further comprising a routine for providing the resolution data set to a reconciler for resolution of the one or more discrepancies.

34. The machine-readable medium as recited in claim 32, further comprising a routine for generating a final image comprising at least one of the one or more resolved discrepancies and the concurrences.

35. The machine-readable medium as recited in claim 32, wherein the two or more respective readers include at least one automated algorithm.

36. The machine-readable medium as recited in claim 32, wherein the discrepancies include at least one of a detection discrepancy or a classification discrepancy.

37. The machine-readable medium as recited in claim 32, wherein the concurrences include at least one of a detection concurrence or a classification concurrence.

38. The machine-readable medium as recited in claim 32, further comprising a routine for providing one or more information cues associated with the one or more discrepancies or concurrences in a resolution image.

39. The machine-readable medium as recited in claim 38, wherein the information cue relates at least one of a statistical measure, a classification description, a prognosis assessment, or a classification provided by a reader.

40. The machine-readable medium as recited in claim 38, wherein the information cue comprises at least one of a visual marker, a text-based message, a numeric assessment, a color coding, or a differential shading.

41. The machine-readable medium as recited in claim 38, wherein the information cue is provided in response to an action by a reconciler.

42. The machine-readable medium as recited in claim 32, wherein the reconciler is one of a human, a partially automated routine, or a fully automated routine.

43. A machine-readable medium, comprising:
a routine for integrating two or more reads of an image data set provided by two or more respective readers, wherein one or more discrepancies exist between the two or more reads; and
a routine for automatically resolving the one or more discrepancies.

44. The machine-readable medium as recited in claim 43, wherein the two or more respective readers include at least one automated algorithm.

45. The machine-readable medium as recited in claim 43, wherein the discrepancies include at least one of a detection discrepancy or a classification discrepancy.

46. The machine-readable medium as recited in claim 43, further comprising a routine for acknowledging the automated resolution results.

47. The machine-readable medium as recited in 43, further comprising a routine for forming a resolution image.

48. The machine-readable medium as recited in claim 47, further comprising a routine for providing one or more information cues associated with one or more discordant features with the resolution image.

49. The machine-readable medium as recited in claim 48, wherein the information cue relates at least one of a statistical measure, a classification description, or a prognosis assessment.

50. The machine-readable medium as recited in claim 49, wherein the information cue comprises at least one of a visual marker, a text-based message, a numeric assessment, a color coding, or a differential shading.

51. The machine-readable medium as recited in claim 49, wherein the information cue is provided in response to an action by a viewer.

52. A method, comprising:
integrating two or more reads of an image data set provided by two or more respective readers to form an integrated data set comprising one or more features; and
reconciling the one or more features of the integrated data set at least partially via an automated algorithm to form a final classification image.

53. The method as recited in claim 52, wherein the two or more respective readers include at least one automated algorithm.

54. The method as recited in claim 52, wherein reconciling the one or more features comprises resolving one or more discrepancies within the integrated data set.

55. The method as recited in claim 54, wherein the discrepancies include at least one of a detection discrepancy or a classification discrepancy.

56. The method as recited in claim 54, wherein one or more concordant features upon which the one or more reads agree are excluded from a resolution image formed to facilitate resolving the one or more discrepancies.

57. The method as recited in claim 52, wherein the reconciler is one of a human, a partially automated routine, or a fully automated routine.

58. The method as recited in claim 52, wherein reconciling the one or more features comprises displaying a concurrence image comprising one or more concordant features within the integrated data set for which the two or more reads agree on at least one of a classification or a detection.

59. The method as recited in claim 58, wherein one or more discordant features are excluded from the concurrence image.

60. The method as recited in claim 52, wherein one or more parties are notified of one or more results found in the final classification image.

* * * * *